United States Patent [19]
Ophir et al.

[11] Patent Number: 5,107,837
[45] Date of Patent: Apr. 28, 1992

[54] METHOD AND APPARATUS FOR MEASUREMENT AND IMAGING OF TISSUE COMPRESSIBILITY OR COMPLIANCE

[75] Inventors: Jonathan Ophir; Youseph Yazdi, both of Houston, Tex.

[73] Assignee: Board of Regents, University of Texas, Austin, Tex.

[21] Appl. No.: 535,312

[22] Filed: Jun. 8, 1990

Related U.S. Application Data

[63] Continuation-in-part of Ser. No. 438,695, Nov. 17, 1989.

[51] Int. Cl.$^5$ .............................................. A61B 8/00
[52] U.S. Cl. ............................................... 128/660.01
[58] Field of Search ...................... 128/660.05, 660.02, 128/661.02, 661.03, 662.03, 774; 73/773, 790

[56] References Cited

U.S. PATENT DOCUMENTS

| | | | |
|---|---|---|---|
| 4,878,500 | 11/1989 | Ophir et al. | 128/660.01 |
| 4,913,157 | 4/1990 | Pratt, Jr. et al. | 128/661.03 |
| 4,947,851 | 8/1990 | Sarvazyan | 128/660.02 |
| 4,976,267 | 12/1990 | Jeffcott et al. | 128/660.01 |

OTHER PUBLICATIONS

Saada, Elasticity, Theory and Applications, Ch. 14. (Pergamon Press, NY, 1974).
Van Pelt, Subtle Tumors Found with New Ultrasound, Insight, May 14, 1990 p. 45.
Levinson, Ultrasound Propagation in Anisotropic Soft Tissues: The Application of Linear Elastic Theory, J. Biomech 20, 251-260 (1987).
Yamokoshi et al., Ultrasonic imaging of itnernal vibration of soft tissue under foced vibration, Proc. Sec. Joint Mtg. of ASA and ASJ, Nov., 1988 (Abstract RR-12).
Boucher et al., Analysis of discrete implementation of generalized cross correlator, IEEE Trans. Acoust., Speech and Sig. Proc. ASSP-29, 609-611 (1981).
Ophir, et al., Elimination of Diffraction error in acoustic attenuation estimation via axial beam translation, Ultrasonic Imaging 10, 139-152 (1988).

Pozniak, et al., Clinical Efficacy of Kitecko Ultrasonic Conductor, Investigative Radiology 24, 128-132 (1989).
Goodman, some fundamental properties of speckle, J. Opt. Soc. Am. 66, 1145-1150 (1976).
Kossoff, et al., A sonographic technique to reduce beam distortion by curved interfaces, Ultrasound Med. Biol. 15, 375-382 (1989).
Eisensher, et al., La Palpation Echographique Rythmec-Echosismographie, Journal de Radiologie 64, 255-261 (1983).
Saada, Elasticity, Theory and Applications, Ch. 14, (Pergamon Press, NY, 1974).
Lerner, et al., Sono elasticity in ultrasonic tissue characteriszation and echographic imaging, in Proc. 7th Eur. Comm. Workshop, J. M. Thijssen, ed. Oct. 1987, Nijmegen, The Netherlands.
Levinson, The Ultrasonic Investigation of Dynamic Muscle Elasticity in Vivo, Abstracts of presentations for the American Institute of Ultrasound in Medicine Proceedings, J. Ultrasound Med., Oct. 1988, Abstract #2005.
Hill, et al., Ultrasound Remote Palpation (URP): Use of Shear Elastic Modulus to Differentiate Pathology, J. Ultrasound Med, Oct. 1988, Abstract #2013.

(List continued on next page.)

*Primary Examiner*—Francis Jaworski
*Attorney, Agent, or Firm*—Arnold, White & Durkee

[57] ABSTRACT

An improved ultrasonic pulse-echo method and apparatus that has particular application in making precision measurements of compressibility in any backscattering material, in particular organic tissue, is disclosed. The method employs a standard transducer or transducer containing device which is translated transaxially, thereby compressing or displacing a proximal region of a target body in small known increments. At each increment, a pulse is emitted and an echo sequence (A-line) is detected from regions within the target along the sonic travel path or beam of the transducer. Resulting time shifts in echo segments corresponding to features in the target provide relative and quantitative information concerning compressibility of the target.

31 Claims, 4 Drawing Sheets

OTHER PUBLICATIONS

Yagi et al., Local Displacement Analysis of Inhomogeneous Soft Tissue by Spatial Correlation of RF Echo Signals, J Ultrasound Med., 1988, Abstract #2028.

Krouskop, et al., Measurement of Stiffness of Soft Tissue Using an Ultrasonic Perturbator, Conference Abstract, Houston Society for Engineering in Medicine and Biology, Feb. 1990, p. 94.

Lerner, et al., Detection of Hard Tumors By Sonoelasticity Imaging: Initial Results, Abstracts, Ultrasonic Imaging and Tissue Characterization Symposium, p. 139 1990.

Gore et al., Dynamic Autocorrelation Analysis of A scans in vivo, Ultrasonic Tissue Characterization II, M. Linzer, ed. NBS, Spec. Publ. 525, pp. 275–280 (U.S. Government Printing Office, Washington, D.C., 1979).

Chu and Raeside, Fourier analysis of the echo-cardiogram, Phys. Med. Biol. 23, 100–105 (1978).

Krouskop et al., A pulsed Doppler ultrasonic system for making noninvasive measurements of the mechanical properties of soft tissue, J. Rehabil. Res. Dev. 24, 1–8 (1987).

Lerner et al., "Sono-elasticity" images derived from Ultrasound signals in mechanically vibrated tissues, Ultrasound Med. Biol. 16, 231–239 (1990).

Tristam, et al., Ultrasonic Study of in vivo kinetic characteristics of human tissues, Ultrasound Med. Biol. 12, 927–937 (1986).

Dickinson and Hill, Measurement of soft tissue motion using correlation between A scans, Ultrasound Med. Biol. 8, 263–271 (1982).

Wilson and Robinson, Ultrasonic measurement of small displacements and deformations of tissues, Ultrasonic Imaging 4, 71–82 (1982).

Parker, K. J., Huang, S. R., Musulin, R. A. and Lerner, R. M., Tissue response to mechanical vibrations for "Sonoelasticity Imaging", Ultrasound Med. Biol. 16, 241–246 (1990).

Tristam et al., Application of Fourier Analysis to Clinical Study of Patterns of Tissue Movement, Ultrasound Med. Biol. 14, 695–707 (1988).

FIG. 8

METHOD AND APPARATUS FOR MEASUREMENT AND IMAGING OF TISSUE COMPRESSIBILITY OR COMPLIANCE

The U.S. Government may own rights in this application and patents that may issue therefrom, pursuant to NIH Grants CA 38515 and CA 44389.

CROSS REFERENCE TO RELATED APPLICATION

This application is a continuation in part of an application entitled "Transaxial Compression Technique for Sound Velocity Estimation," Ser. No. 7/438,695, filing date Nov. 11, 1989.

Applicant incorporates said application Ser. No. 7/438,695 by reference herein and claims the benefit of said application for all purposes pursuant to 37 C.F.R. §1.78.

BACKGROUND OF THE INVENTION

1. Field of the Invention

This invention relates generally to methods and apparatus for performing ultrasonic diagnosis of a target body. More particularly, the invention pertains to methods and apparatus for measuring compressibility or compliance in a target body. The invention is directed towards techniques for enhancing the accuracy of such measurements in compressible or compliant targets, particularly the human body, using one or more ultrasonic transducers in pulse-echo mode.

2. Description of Related Art

Traditional ultrasonic diagnosis is achieved by transmitting ultrasonic energy into a target body and generating an image from the resulting echo signals. A transducer is used to both transmit the ultrasonic energy and to receive the echo signals. During transmission, the transducer converts electrical energy into mechanical vibrations. Acquired echo signals produce mechanical oscillations in the transducer which are reconverted into electrical signals for amplification and recognition.

A plot or display (e.g., on an oscilloscope, etc.) of the electrical signal amplitude versus echo arrival time yields an amplitude line (A-line) or echo sequence corresponding to a particular ultrasonic transmission. When the A-line is displayed directly as a modulated sinusoidal pattern at radio frequency ("RF"), it is typically referred to as an RF or "undetected" signal. For imaging, the A-line is often demodulated to a non-RF or "detected" signal.

Ultrasound techniques have been extensively used in the field of diagnostic medicine as a non-invasive means of analyzing the properties of tissue in vivo (i.e., living). A human or animal body represents a nonhomogeneous medium for the propagation of ultrasound energy. Acoustic impedance changes at boundaries of regions having varying densities and/or sound speeds within such a target body. At such boundaries, a portion of the incident ultrasonic beam is reflected. Inhomogeneities within the tissue form lower level scatter sites that result in additional echo signals. Images may be generated from this information by modulating the intensities of pixles on a video display in proportion to the intensity of echo sequence segments from corresponding points within the target body.

Conventional imaging techniques are widely used to evaluate various diseases within organic tissue. Imaging provides information concerning the size, shape, and position of soft tissue structures using the assumption that sound velocity within the target is constant. Qualitative tissue characterization is carried out by interpretation of the grey scale appearance of the sonograms. Qualitative diagnosis largely depends on the skill and experience of the examiner as well as characteristics of the tissue. Images based only on relative tissue reflectivity, however, have limited use for quantitative assessment of disease states.

Techniques for quantitative tissue characterization using ultrasound are needed for more accurate diagnosis of disorders. In recent years many significant developments have been achieved in the field of ultrasonic tissue characterization. Some acoustic parameters, e.g., speed of sound and attenuation, have been successfully used for tissue characterization. One promising physical parameter for quantitative measurement is compressibility or compliance. The amount of compressibility or compliance within tissues changes within regions of varying density. Diseased tissue, such as tumors, may be harder or softer than normal tissue, and thus have a different amount of compressibility.

Tissue compressibility is an important parameter which is used to detect the presence of diffuse or localized disease. Measuring changes in compressibility becomes important in the analysis of tissue for pathological conditions. Many tumors are firmer than the surrounding normal tissue, and many diffuse diseases result in firmer or more tender pathology. Examples can be found in diffuse liver disease, prostate cancer, uterine fibroids, muscle conditioning or disease, and many other conditions.

Traditionally, physicians routinely palpate various regions of a patient's body to get an impression of tissue firmness or tissue softness. This technique is a form of remotely trying to sense what is going on in terms of tissue compliance. For example, in a liver, if the compliance in an area is sensed to be different from compliance in the surrounding area, the physician concludes from the tactile sensations in his fingers that something is wrong with the patient. The physician's fingers are used to perform a qualitative measurement.

The ability to quantitatively measure the compressibility or compliance of tissue in localized regions would help with (1) objective quantification of commonly used clinical signs, (2) localizing these measures, (3) making the measurements deep in tissue with simple equipment, (4) constructing images of the compressibility or compliance parameter in vivo, which may be used alone or in conjunction with ordinary sonograms.

One technique has attempted to quantitatively measure the elasticity and compressibility of tissues by correlating patterns obtained in ultrasonic measurements of tissue movement in vivo. The method applies Fourier analysis to a clinical study of patterns of tissue movement, specifically in the liver. The technique uses Fourier analysis to enable objective differentiation of different tissue types in pathologies on the basis of numerical features of the time-course of the correlation coefficient between pairs of A-scans recorded with a particular time separation. Tissue oscillations resulting from periodic stimulus by waves resulting from ventricular contraction and pressure pulses in the descending aorta are measured to derive patterns of movement. Fourier series transformation is used to analyze the data to quantitate the kinetic behavior of the tissue in vivo. See. Tristam et al.. "Application of Fourier Analysis to Clinical Study of Patterns of Tissue Movement," Ultrasound in Med. & Biol., Vol. 14, No. 8, (1988) 695-707.

In another approach, patterns of tissue movement are correlated in vivo. This technique basically studies details of the patterns of movement in tissues in response to a normal physiological dynamic stimulus such as cardiac motion. A method is given for quantifying tissue movement in vivo from the computation of a correlation coefficient between pairs of A-scans with appropriate time separation. Tristam et al., "Ultrasonic Study of in vivo Kinetic Characteristics of Human Tissues," Ultrasound in Med. & Biol., Vol. 12, No. 12 (1986) 927-937.

The waveforms of liver dynamics caused by aortic pulsation and vessel diameter variations are analyzed in still another method, involving a signal processing technique for analyzing radio frequency M-mode signals. The technique uses patterns of movement in response to arterial pulsation to determine tissue characteristics. The technique measures displacement, velocity, and strain as a function of time in small deformations in tissue due to arterial pulsation. Wilson and Robinson, "Ultrasonic Measurement of Small Displacements and Deformations of Tissue," Ultrasonic Imaging, Volume 4, (1982) 71-82.

Yet another method processes echoes in order to measure tissue motion in vivo. The motion patterns observed in vivo are correlated to arterial pressure pulse. Dickinson and Hill, "Measurement of Soft Tissue Motion Using Correlation Between A-Scans," Ultrasound in Med. & Biol., Vol. 8, No. 3, (1982) 263-271.

All of the above techniques focus upon the dynamic motions of tissue in vivo. These methods are limited due to the complexity of tissue motion, and the behavior of the stimuli employed in those methods.

SUMMARY OF THE INVENTION

The present invention provides a pulse-echo system that has particular application in estimating compressibility in a target body. The target body may be any animal or human tissue, or any organic or inorganic substance that is compressible or compliant. The term "animal tissue" includes "human tissue". An ultrasonic source is used to interrogate the target body. The detection of echo sequences may be at the ultrasonic source. The invention allows for accurate, localized determination and imaging of an important parameter, compressibility, which has been used qualitatively in medicine for a very long time.

The compressibility of a material is normally defined as the inverse of the bulk modulus of the material. Thus, compressibility = $(v/V)/(F/a)$ where
v = a change in volume;
V = the original volume;
F = force applied to the volume;
a = area across which the force is applied.

In the present instance, it may be generally assumed in determining relative compressibilities within a material that the terms "F" and "a" will remain constant along an axis of compression, and that the terms "l" and "L" may be employed in place of v and V, where
l = a change in the length of a segment of interest along an axis of compression, and
L = the original length of the segment.

Thus, the compressibility of any given segment or layer within a material relative to another segment or layer may be estimated from the relationship $K_1 = K_2 (l_1/L_1)/(l_2/L_2)$, where $K_1$ = compressibility of a first segment or layer;
$l_1$ = change in length of the first segment or layer along an axis of compression in response to a given force;
$L_1$ = original length of the first segment;
$l_2$ = corresponding change in length of a second segment or layer;
$L_2$ = original length of the second segment or layer; and
$K_2$ = compressibility of the second segment or layer.

In those instances where absolute value of compressibility of a segment or layer is desired, such a value may be estimated from the relationship compressibility = $(l/L)/(F/a)$ where
F = a change in compressive force, and
a = the area of application—typically, the cross-sectional area of a transducer forced against a material which includes the segment or layer of interest.

In the present invention, the velocities of sound in different segments or layers may be employed, together with time measurements, to calculate distances within the segments or layers. The ultrasonic signals also provide a precise measuring tool. The velocities of sound may be determined using the apparatus and procedures disclosed in the application entitled "Transaxial Compression Technique for Sound Velocity Estimation," Ser. No. 7/438,695, filing date Nov. 17, 1989.

The invention contemplates sonically coupling an ultrasonic source to a target body; energizing the ultrasonic source to emit a first ultrasonic signal or pulse of ultrasonic energy from the source along an axis into the target body; detecting from a region within the target body a first echo sequence including a plurality of echo segments resulting from the first transmitted signal; displacing the target body along the axis while maintaining coupling between the ultrasonic source and the target body; energizing the ultrasonic source to emit a second ultrasonic signal along the axis into the target body; and detecting from the region within the target body a second echo sequence including a plurality of echo segments resulting from the second transmitted signal; measuring the differential displacement of the echo segments. A plurality of first ultrasonic signals or pulses of ultrasonic energy may be emitted and a plurality of first echo sequences detected before displacing the target body. Then a plurality of second signals and pulses are emitted along a plurality of parallel paths and a plurality of second echo sequences are detected.

In one embodiment, a transducer is the ultrasonic source and is sonically coupled to direct an ultrasonic signal or pulse of ultrasonic energy into the tissue along a radiation axis such that movement of the transducer along the axis effects a change in compression of the tissue.

In a preferred embodiment of the present invention, the ultrasonic source is a transducer sonically coupled to a tissue of interest. A first pulse of ultrasonic energy is emitted along a path into the target body and the arrival of a first echo sequence (A-line) including one or more echo segments is detected from regions within the tissue along the path resulting from the first pulse of ultrasonic energy. Thereafter, compression is changed within the tissue along the path. The compression change may be accomplished by transaxially moving the transducer along the path to compress or displace a proximal region of the tissue. A second pulse is emitted, and the arrival of a second echo sequence including one or more echo segments common to the first echo sequence is detected in response to the second pulse. The differential displacements of at least one echo segments is measured. The echo sequences detected are from common regions within the tissue.

A comparison of the first and second echo sequences or waveforms with intervening compression reveals a generally decreasing displacement of tissue structures with depth. In a homogeneous medium, the rate of decrease will tend to be asymptotic. Of particular interest is the differential displacement per unit length—i.e., strain. In a homogeneous compressible medium, the strain will tend to be constant along the axis of displacement. In a non-homogeneous medium, the strain varies along the axis of displacement.

The strain of a tissue may be calculated using the arrival times of first and second echo sequences from proximal and distal features in a target body—i.e., tissue—using the following equation:

$$\frac{(t_{1B} - t_{1A}) - (t_{2B} - t_{2A})}{(t_{1B} - t_{1A})}$$

$t_{1A}$ = arrival time of a first echo sequence from a proximal feature;
$t_{1B}$ = arrival time of a first echo sequence from a distal feature;
$t_{2A}$ = arrival time of a second echo sequence from a proximal feature; and
$t_{2B}$ = arrival time of a second echo sequence from a distal feature.

The arrival times of the echo segments from a common point detected in response to a first and second pulse of ultrasonic energy are compared. The common points may be found in features occurring within the echo signal. The time shifting of the two echo segments is used to determine compressibility.

Thus, if no change in arrival time has occurred with an intervening compressive force, it follows that a target body has not been compressed along the travel path leading to the source of the echo segments. On the other hand, if the arrival time of the second echo segment is smaller than the arrival time of the first echo segment, it is clear that compression has occurred and that the target body is compressible. Moreover, the difference in arrival times, taken together with other available data, makes it possible to quantify the compressibility of the target body.

In another embodiment of the invention, body segments which extend along the transmission path of the ultrasonic pulses are selected within a target body and separate first and second echo segments detected from within each body segment. Thus, a series of first and second echo segments is detected for the body segments selected for interrogation. Preferably, the echo segments are detected from the proximal and distal ends of body segments relative to the ultrasonic source. Measurement of the time shifts of echo segments in the first and second echo sequences which correspond to the proximal and distal ends of each body segment are then made. By studying the time shifts, it becomes possible to determine whether changes in compressibility occur along the ultrasonic beam within the target body.

A preferred embodiment of the invention involves (1) sonically coupling a material with a known Young's Modulus and speed of sound to the surface of the target body; (2) emitting a first pulse of ultrasonic energy along a path through the material into the target body; (3) detecting a first echo sequence including a plurality of echo segments, from within the target body resulting from the first pulse; (4) forcing the material against the target body sufficiently to displace the target body while maintaining acoustic coupling between the material and the target body; (5) emitting a second pulse of ultrasonic energy along the path through the material into the target body; and (6) detecting a second echo sequence including a plurality of echo segments common to the first echo sequence, resulting from the second pulse. The presence of the material with a known Young's modulus and speed of sound makes it possible to determine the Young's modulus of the target body. If the target body, itself, has multiple layers, it also becomes possible to determine the Young's moduli of the individual layers. The application of Young's modulus to these matters is explained later in this description.

The present invention takes advantage of the acoustical properties of physically compressible or displaceable materials. These materials—for example, animal or human tissues—often contain a large number of acoustic "scatterers". The scatterers, being small compared to the wavelength of the sound frequencies involved, tend to reflect incident sound energy in all directions. For example, in homogeneous tissue regions, scatterers may comprise a collection of nearly identical reticulated cells. The combined reflections from each scatterer create a background echo signal called speckle. A particular arrangement of scatterers will shift in response to axial forces from the transducer, changing the time an echo is received from the arrangement. The echoes received from the various arrangements of scatterers form an echo sequence. A selected echo segment or wavelet of the reflected RF signal corresponds to a particular echo source within the tissue along the beam axis of the transducer. Time shifts in the echo segment or wavelet are examined to measure compressibilities of tissue regions. It is important that the shape of the echo segment or wavelet not change significantly, due to compression, such that identification of the wavelet is not possible, and that the signals not be decorrelated beyond an acceptable range. The time shift can be determined by analyzing the data in a computer or by a visual examination, but the analysis will generally be easier with a computer.

Studying an internal region of the human body is accomplished by sonically coupling an ultrasonic transducer to the body so as to emit an ultrasonic signal along an axis into the region, and such that movement of the transducer along the axis relative to the region will change the compression of the body between the transducer and the region; energizing the transducer to emit a first signal along the axis into the body and the region; detecting the arrival at the transducer of a plurality of spaced echo segments resulting from the first signal and coming from the region; moving the transducer along the axis relative to the region sufficient to change the compression of the body between the transducer and the region while maintaining said sonic coupling; energizing the transducer to emit a second signal along the axis into the body and said region; detecting the arrival at the transducer of each echo segment resulting from the second signal; and determining the strains produced in segments of the region between the pairs of echo segments.

The present invention is of particular interest in interrogating organic tissue, especially human and other animal tissue. Thus, as a transducer is pressed against such a material, scatterers in a region within the material are displaced from one position to another. For elastic materials, release of the pressure enables the scatterers to return to their original position. A principal object of such interrogation is to use echo signals from the tissue in strain studies which may reveal the presence of abnormalities. In general, when employing a transducer to transmit signals into a living body, care should be taken to coordinate the transducer signals with naturally occurring signals. Thus, in the human body, the transducer should normally be activated at times which will minimize interference by signals such as aortic and vessel pulses.

This invention may be used in the detection of diseases such as breast cancer and prostate cancer to accurately detect and locate tumors at an early stage. Another advantage of the invention is the avoidance of ionizing radiation from x-rays.

It will be noted at this point that the invention is contemplated to have significant applications other than in medicine. One such application, for example, is in the quality grading of beef. The invention may be used to quantitate the tenderness of beef before and after slaughter. This ability is economically important in determining when to slaughter cattle. Other applications would include, for example, interrogation of materials and products such as cheese or crude oil that are physically displaceable by the movement of a transducer.

It will be noted that the transducers employed in the present invention need not be in direct contact with the materials to which they are applied. It is necessary, however, that transducers be sonically coupled to the materials in a manner such that movement of the transducers will result in displacement of the materials. Sonic coupling methods and agents are well known in the art.

It will be also noted that a material may be displaced according to the invention either (a) by advancing a transducer against a compressible elastic material to increase compression, or (b) by retracting a transducer from a compressed position within the material. Changing compression means compressing or decompressing the target body.

As noted above, it is not necessary that an echo from a discrete feature in a tissue or other compressible material be employed. It is sufficient that an identifiable echo segment be present in the echo signal resulting from a transmittal signal. Even though the physical features within a material responsible for a selected echo segment may not be clearly known, the selected echo segment is an adequate reference for the purposes of the invention. Thus, the compression of a material and signal travel times determined before and after such compression may be based upon comparison of time shifts in the echo segments. Similarly, the recovery of an elastic material from an initially compressed condition and the signal travel times before and after such recovery or decompression may be based upon comparisons of time shifts in the echo segment.

The present invention may also be employed for estimating compressibility or compliance in targets having multiple layers. It will be noted that the terms "compressibility" and "compliance" in the present context have generally similar connotations. In any event, the compressibility in each of the progressively deeper layers is estimated by employing the same techniques discussed above. According to the present invention, the compressibility may be estimated in each layer from only two echo sequences along the axis of radiation. The echo sequence may be divided into echo segments corresponding to the layers. Thus, imaging of the compressibility parameter in a plane or volume of a target body may also be accomplished by appropriate lateral translation of the transducers. Other objects and advantages of the invention will become readily apparent from the ensuing description.

BRIEF DESCRIPTION OF THE DRAWINGS

FIG. 1b shows a plot of an RF echo signal originating from the distal tissue region interrogated in FIG. 1a.

FIG. 2b shows a plot of the time shifted RF echo signal originating from the distal tissue region as interrogated in FIG. 2a.

DETAILED DESCRIPTION

Figure 1A:
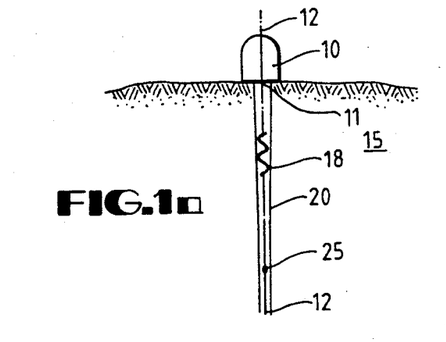
FIG. 1a shows an embodiment of the invention where one transducer is sonically coupled to a target body to interrogate a distal tissue region within the target body.
Figure 1B:
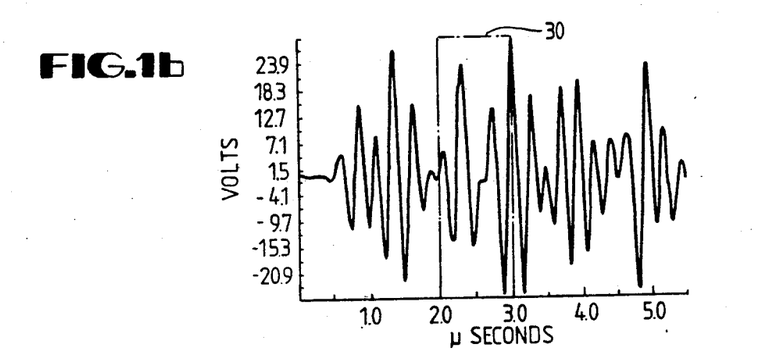

FIG. 1a shows the transducer 10 sonically coupled to a target body 15. An ultrasonic pulse 18 is shown propagating within beam 20 toward a echo source 25 on beam axis 12. As the pulse 18 propagates through the target 15, corresponding echoes are generated and arrival times noted at the transducer aperture 11. The combination of all echoes generated from reflections within the beam 20 is the echo sequence or A-line corresponding to pulse 18. A radio frequency ("RF") signal plot of the A-line acquired from pulse 18 is shown in FIG. 1b. The amplitude of the signal in millivolts is plotted against echo arrival times in microseconds ($\mu$s). Later arrival times correspond to progressively deeper regions within the target body 15. An echo segment or echo wavelet 30, within a chosen arrival time Window, is selected as a reference. The time window may be selected based on anatomical data from ultrasound imaging, or may be arbitrary, e.g., every x micro seconds. The echo segment or wavelet 30 originates from the echo source 25.

Figure 2A:
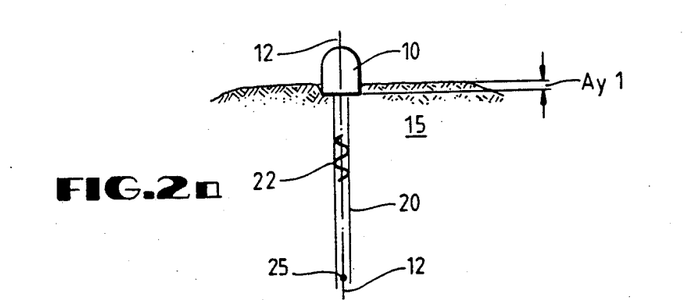
FIG. 2a shows the transducer of FIG. 1a imparting a small compression to a proximal region of the target body.
Figure 7:
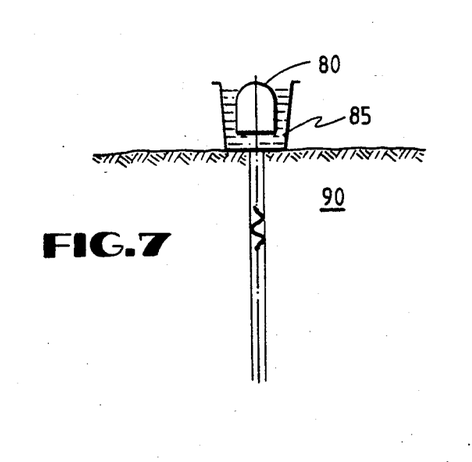
FIG. 7 shows an apparatus embodiment of the invention in which a transducer is coupled to a target body via a stand-off device containing an acoustic coupling fluid.

FIG. 2a shows the transducer 10 being translated along axis 12 to impart a small compression ($\blacktriangle y_1$) to the tissue. Alternatively, as shown in FIG. 7, a transducer 80 may be associated with a stand-off device 85 which allows the transducer so to be acoustically or sonically coupled to the target body 90 without being in direct contact with the target body. In this case the stand-off 85, and not the transducer, compresses the target.

Figure 2B:
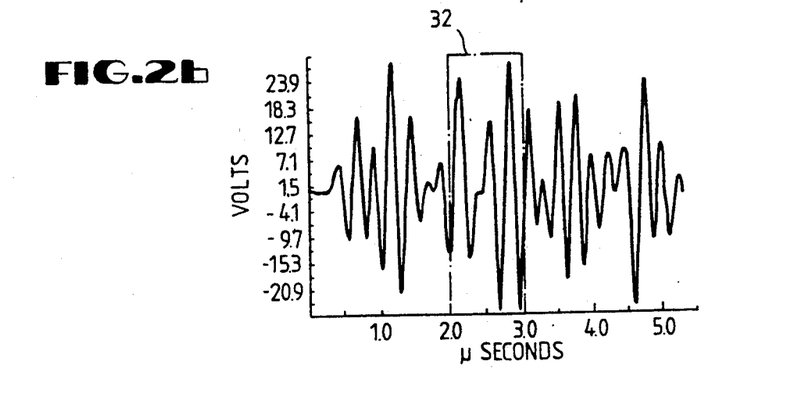

After the transducer 10 Compresses the target, a second pulse 22 is emitted and the corresponding A-line segment is acquired from a desired depth within the tissue. FIG. 2b shows the RF plot of a time shifted A-line corresponding to pulse 22. The echo segment or wavelet 32 associated with echo source 25 is also time shifted. The time shifted wavelet 32 is tracked within the selected time window using standard pattern matching techniques. The window selected must be such that the wavelet of interest will not be shifted out of the window. This selection may involve the size of the window or the positioning of the window. The window selected should reveal both wavelets or echo segments. The arrival time of echo segment or wavelet 32 is prior to that of echo segment or wavelet 30 above, since the distance between aperture 11 and feature 25 was shortened by the compression $\Delta y_1$.

In a preferred embodiment of the invention, a transducer is positioned on or otherwise coupled to a target tissue and advanced axially toward the target to compress the target. Alternatively, the invention may be practiced by retracting a transducer from a previously compressed position. Since the relatively large aperture size of the transducer precludes penetration of the tissue, small tissue displacements occur instead. A pulse is emitted prior to the displacement, and a first echo sequence received in response to the pulse is recorded. Following displacement, a second pulse is emitted and a second echo sequence is recorded in response to transmission. Next, a comparison of the waveforms is made to reveal a decreasing displacement of the tissue structures with depth. The decrease will generally be asymptotic in character.

In the foregoing embodiment, a single compression of a homogenous target body, and a repetitive sinusoidal waveform signal have been described. It will be apparent, however, that other conditions may be employed. Thus, multiple compressions, other waveforms and other signal sources, such as array transducers, may be used. These signal sources, for example may be non-repetitive and may generate spike-like signals.

In tissue that is not homogeneous, the shifting of tissue in various segments will differ. For example, if a segment of tissue is less compressible than the overall tissue containing the segment, the tissue in the segment will compress or strain less than if the segment of tissue were of the same compressibility as the tissue as a whole. Alternatively, when a segment is more compressible than the tissue as a whole, the segment will compress or strain more than if the segment were of the same compressibility as other segments.

Figure 3:
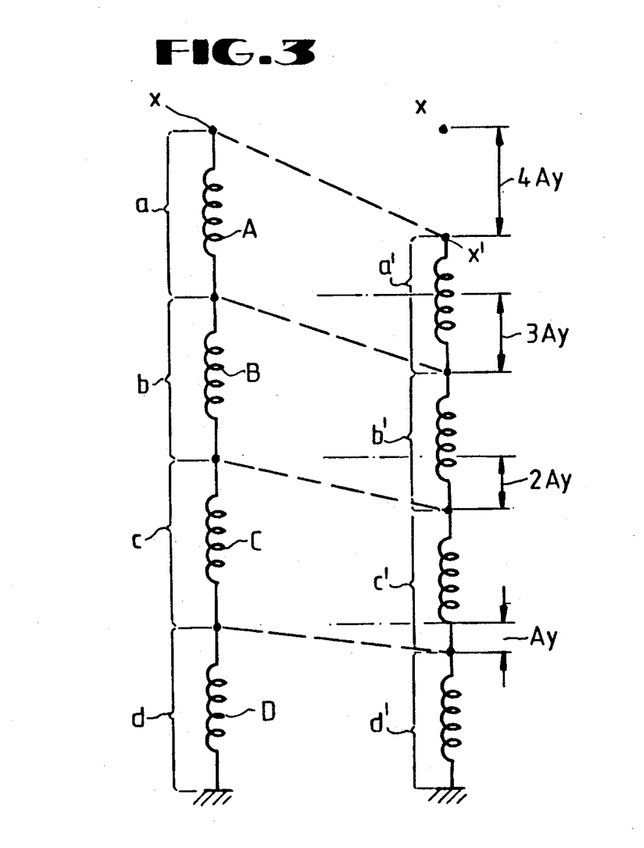
FIG. 3 shows a one dimensional spring model of tissue before and after compression.

Referring to FIG. 3, a strain model is shown which illustrates how Young's Modulus may be employed in explaining the application of the present invention to compressible materials, notably human organs and tissue. Young's modulus is a basic property of elastic materials and elastic materials can be characterized by their Young's moduli. Human tissue, accordingly, may be similarly described.

Briefly stated, Young's Modulus for any given material is the numerical ratio of the stress applied to the material to the resulting strain in the material. Thus, $Y=F/(A)(S)=P/S$, where Y is Young's Modulus for a given material; F is the total force applied to the material; A is the area of application of the force; S is the strain; and P is pressure. It will be recognized from the relationship of these several factors that the Young's modulus of a material is a measure of the stiffness of the material.

The model in FIG. 3 represents four segments A, B, C and D of a compressible body wherein each segment is uniformly compressible and equal in length when not compressed. Each segment in FIG. 3 is represented by a spring which is identical to the other springs. The springs in the left hand array reflect the condition of the model at a state of no compression. The springs in the right hand array represent the condition of the model when a compressive force applied to the top most segment has displaced the top of that segment by a distance $4\Delta y$. It may be seen that point x has been displaced by a distance $4\Delta y$ to point x'. It may also be seen that this total displacement has been distributed equally across each one of the springs, thereby causing each segment to shorten by the same amount. Thus, segment or spring A has been shortened by $\Delta y$ from a to a'; segment or spring B has been shortened by $\Delta y$ from b to b', etc. The net effect, however, has been to displace each segment progressively more, going from segment or spring D to segment or spring A.

The total compression of the model is shown by the change in length $4\Delta y$. The change in length of segment A is calculated as $4\Delta y - 3\Delta y = \Delta y$. The total compression of segments B-D is shown by the change in length $3\Delta y$. The change in length of segment B is calculated as $3\Delta y - 2\Delta y = \Delta y$. The total compression of segments C and D is shown by the change $2\Delta y$. The change in length of segment C is calculated as $2\Delta y - \Delta y = \Delta y$. Finally, the total compression of segment D is shown by the change in length $\Delta y$ from d to d'. The change in length of segment D is calculated as $\Delta y - 0 = \Delta y$. The change in length of each segment is equal to $\Delta y$. Each segment, as long as all of the segments are equal in compressibility, compresses by the same net amount $\Delta y$.

The strain of each segment may be computed as $\Delta y/1$, where 1 is the initial (uncompressed) length of the segment. This strain value is in fact the quantity of most interest for purposes of display. Clearly in this case, the strain in this one-dimensional system is constant for each segment, reflecting the fact that all springs are equal. The strain is, however, affected by the initial displacement.

Figure 4:
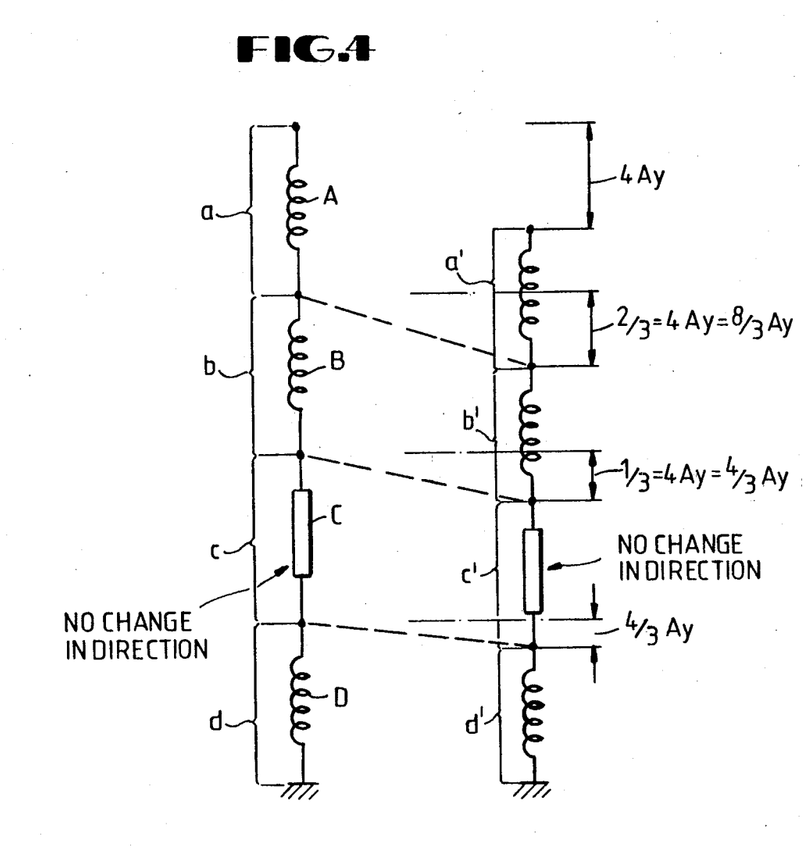
FIG. 4 shows a one dimensional spring model of tissue with a totally incompressible section before and after compression.

On the other hand, if a segment in the above strain model were totally incompressible, the incompressible section would show no strain, but its presence would nevertheless affect the compression of the other sections. Referring to FIG. 4, for example, one of the springs C in the model of FIG. 3 has been replaced by a totally stiff spring (so stiff, it can actually be replaced by a thin rod which is incompressible). Now one of the segments is incompressible. Using the same total compression in FIG. 3 of $4\Delta y$, the total compression of segments A-D is shown by change $4\Delta y$ in overall length. The change in length for Segment A is now calculated as $4\Delta y - \tfrac{8}{3} \times 4\Delta y = 4(1\tfrac{1}{3})\Delta y = (4/3)(\Delta y)$.

The total compression of segments B-D is shown by the change $(8/3)(\Delta y)$ in overall length. The change in length of segment B is now calculated as $8/3\Delta y - 4/3\Delta y = (4/3)(\Delta y)$.

The total compression of segment C is zero. The change in length for segment C is calculated as $(4/3)(\Delta y) - (4/3)(\Delta y) = 0$.

The total compression of segment D is shown by the change in length from d to d'. The change in length of segment D is calculated as $(4/3)(\Delta y) - 0 = (4/3)(\Delta y)$.

Each of the segments A, B, and D is compressed equally, since they are represented by equal springs. However, the amount by which each one of these segments is compressed is larger than in the prior example, because the same displacement $4\Delta y$ is now divided over 3 springs, and not 4 as before. The segment C, represented by a incompressible rod shows no strain, but its presence affects the compression of the others. 0 In conclusion, as long as segments, represented by springs, have the same Young's modulus, they will show equal strain which may be measured. The magnitude of this strain is dependent on the initial compression and on the number of equal segments. A segment of different Young's modulus can be discerned due to the different strain effects it introduces. Its presence changes the strains of the surrounding segments. Thus, changes in strain within different segments of a tissue may be detected by using a spring model of the tissue.

As explained above, the presence of an abnormality or defect in an otherwise homogeneous tissue causes the baseline strain of the surrounding homogeneous segments to change, because of the requirement that the integral of all the strains along the strain path (area under strain profile) be equal to the initial displacement. In other words, "normal" tissue strain is influenced by the size and Young's modulus of an abnormal segment. Thus, only relative measurements can be made using the strain model alone. These measurements are useful, but absolute measurements are also desirable.

It becomes possible to determine compressibility within a tissue in absolute terms using a strain profile which includes the tissue together with a coupling medium with a known Young's modulus and speed of sound. Thus, a layer of a material having a known Young's modulus and speed of sound may be interposed as a layer between a transducer and the tissue, and the method of the invention may then be applied to obtain a strain profile of the combined layers. The known layer may consist of compressible or compliant material such as rubber, sponge, gels, etc. The material should be compressible and provide for an ultrasonic transmission path to the tissue. The material may be echogenio, but it is not necessary.

Using the method of the invention, sonic measurements are made before and after a force is applied to a transducer so as to compress the known layer and the unknown tissue. The resulting strain data are used to produce a strain profile. The strain measurements may then be converted to Young's Modulus measurements by calculating the force per from the distal tissue region interrogated in FIG. Ia. unit area ("stress"). Thus, the additional strain from the layer of known material is used to calculate the stress with the formula.

Stress of the known layer = Young's modulus of the layer x the measured strain in the layer.

Once the stress is known, the Young's Modulus for the unknown tissue may be readily obtained, since the force is the same along the whole area of compression, and the area is also the same.

Thus, a strain profile can be converted to a Young's modulus profile which is absolute, and which is independent of the presence of defects or the amount of compression. Essentially, the overlying layer acts as a "stress meter". This also allows compression of the tissue in an arbitrary way, since the results will be independent of the initial compression, as long as the linear behavior of the tissue is maintained.

FIG. 7 shows an apparatus for determining compressibility of a target body (204) comprising a rigid frame (199); a motor (200) attached to the frame (199); an axial member (201) having a first and second end, the first end being coupled to the motor (200) such that the axial position of the axial member (201) can be varied by operating the motor (200); and an ultrasonic source (202) mounted on the second end of the axial member (201). The ultrasonic source (202) has a surface capable of being sonically coupled to the target body (204).

The ultrasonic source (202) may be a single transducer or a transducer array. A gated transducer array is preferred when using a transducer array. Also, the axial member (201) may be a worm gear.

The top surface of a layer (203) with a known Young's modulus and speed of sound may be coupled to the ultrasonic source's (202) lower surface (212). The bottom surface of the layer (203) is coupled to the target body (204).

The apparatus may also contain a data storage medium connected to the transducer for storing signals from the transducer. The movement of the axial member (201) may be controlled in precise amounts by using a motor controller (205) connected to the motor (200), such that operation of the motor (200) moves the axial member (201) in precise amounts.

Figure 8:
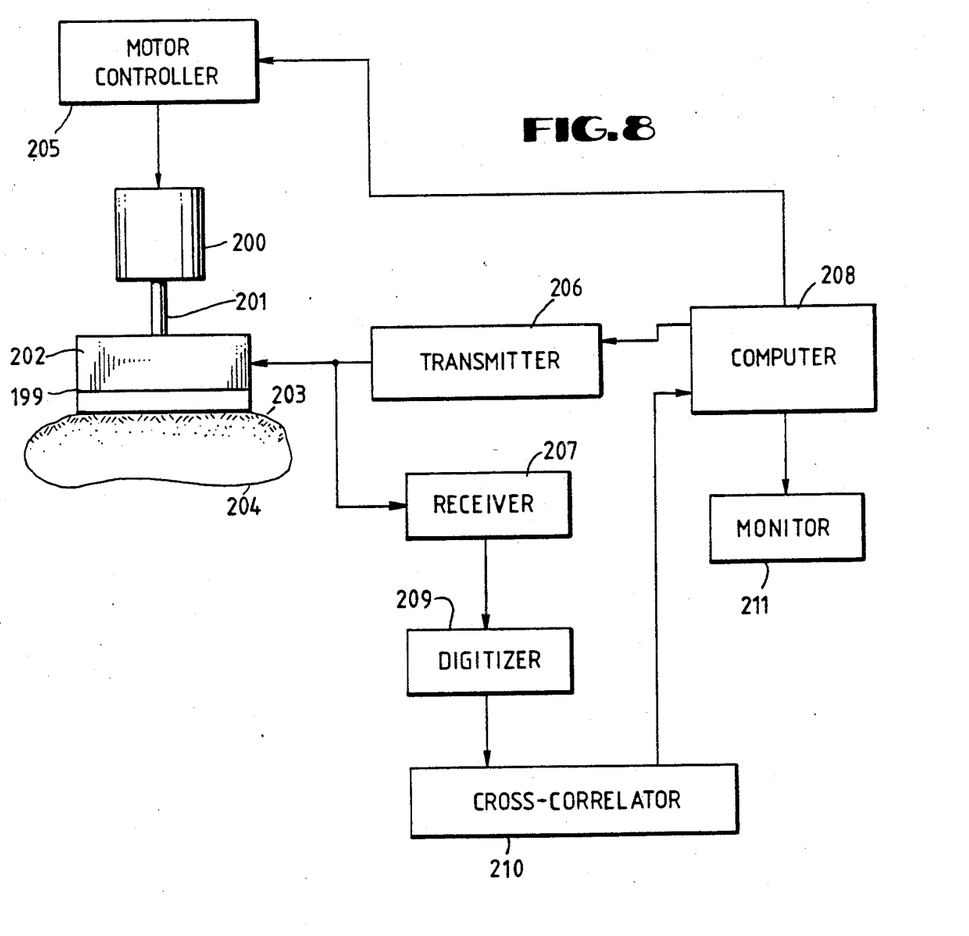
FIG. 8 is a block diagram depicting an apparatus embodiment of the invention controlled by a computer.

A transmitter (206) may be connected to the ultrasonic source (202) to energize the ultrasonic source (202). A receiver (207) may also be connected to the ultrasonic source (202) such that signals generated by the ultrasonic source (202) in response to echo sequences are transmitted to the receiver (207). A digitizer (209) may be connected to the receiver (207) to convert analog signals into numerical data. Furthermore, a cross-correlator (210) may be connected to the digitizer (209). A computer (208) may be connected to the transmitter (206) such that the computer (208) is capable of triggering the transmitter (206). Also, the cross-correlator (210) may be connected to the computer (208) such that data may be received by the computer (208). The computer (208) may be programmed to convert the echo sequences into a strain profile or into a Young's modulus profile. Images of the strain profile and the Young's modulus profile may be displayed on a monitor (211) connected to the computer (208).

Although the apparatus and method of this invention have been described in relation to clinical diagnosis, this should be understood not to be a limiting factor on the utility of the invention. For example, the present invention may be used in forensics, tissue characterization studies, veterinary medicine, laboratory experiments, and industrial applications. Also, the present techniques may be employed to any materials that are capable of being physically compressed or displaced. That is, a material which is internally displaceable in response to pressure applied to the material.

The various aspects of the invention will appear more specifically in the following examples that are purely illustrative and should not be construed to limit the scope of the invention.

EXAMPLE 1

Figure 5:
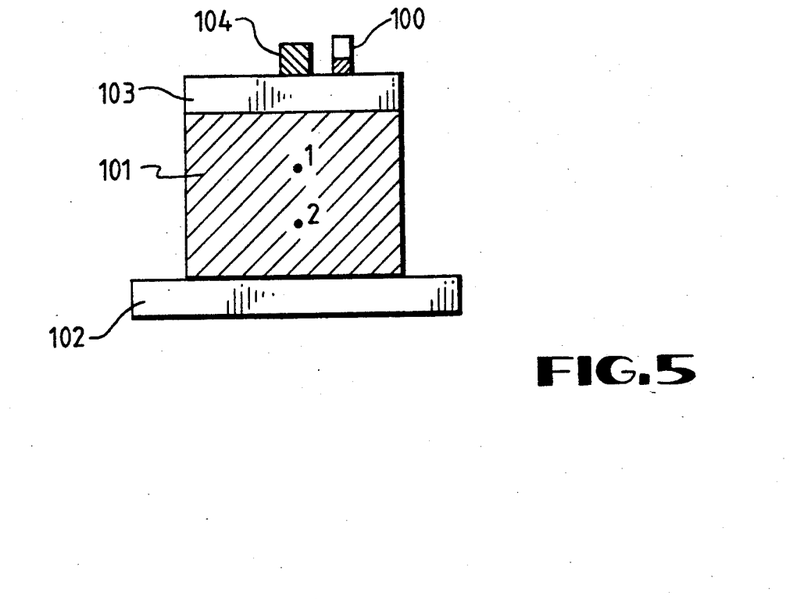
FIG. 5 shows the equipment set up for experiment 1.

Referring to FIG. 5, a water tank experiment was conducted to test the method of estimating relative compressibilities using a simulated tissue or tissue "phantom". A rectangular polyester sponge tissue phantom 101 whose size was 188 mm × 88 mm × 45 mm was placed in a beaker, and distilled water was added to completely immerse the phantom 101. The beaker was placed in a desiccator, and laboratory vacuum was applied for approximately 15 minutes. Thereafter, the beaker was submerged in a distilled water tank, and the phantom 101 was removed and placed on a 6.35 mm thick polished stainless steel reflector 102. The phantom 101 was allowed to reach a temperature equilibrium of 37.0±0.5 degrees C. Sponge phantoms under these conditions have been found to simulate human tissue very effectively.

A thick plexiglass plate 103 having a surface area equal the top surface area of the phantom 101 was placed on top of the phantom sponge. The thickness of the plexiglass plate 103 was 15 mm. The thick plexiglass plate 103 was used to prevent or reduce elastic deformation of this layer.

To determine compressibility of the sponge phantom, a weight 104 was placed on the plexiglass plate and positioned to make the weight 104 center near the center of the plate 103. The transducer 100 was then coupled to the plexiglass plate 103. Next, the shift times of signals backscattered from targets 1 and 2 before and after placing weight 104 on plate 103 were obtained. The process was repeated ten times and the average values were used for calculation. Buoyancy effects were taken into account.

The strain was determined to be $4.56 \times 10^{-3}$. Since the force applied by weight 104 was 3.43N (0.35 Kg) and the top surface area of phantom 101 was $18.8 \times 8.8$ cm$^2$, the stress on unit area was 0.021N/cm$^2$. The Young's modulus of the absolute phantom was calculated to be 4.54N/cm$^2$.

EXPERIMENT 2

Figure 6:
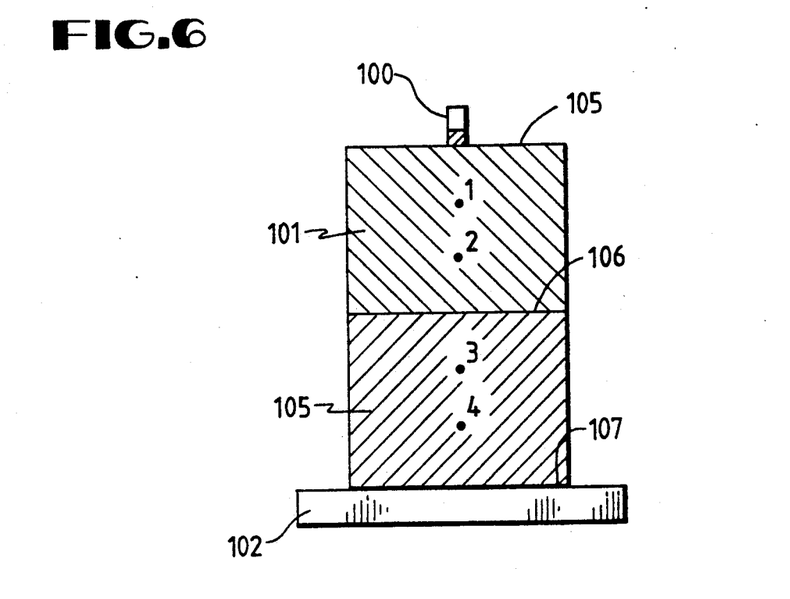
FIG. 6 shows the equipment set up for experiment 2.

The equipment setup for this experiment, shown in FIG. 6, was used to test the ability of the present invention to measure relative compressibilities of different tissues. In addition, a second phantom formed from a foam layer was added to the setup. The second foam layer was constructed with a compressibility different from the first sponge tissue phantom. The second phantom ("phantom 2") 105 was more compressible than the first phantom ("phantom") 101. For measuring the relative deformation of segments 1, 2 and 3, 4 the time shift of signals backscattered from targets 1, 2, 3 and 4 were each recorded. The respective arrival times of $t_1$, $t_2$, $t_3$ and $t_4$ were 30 μs, 50 μs, 80 μs and 100 μs. transducer 100 was moved in 0.5 mm increments toward the proximal simulated tissue region. Each time shift was obtained by averaging the data from ten measurements. For reference, the absolute compressibilities of two phantoms 101; 105 were separately determined by using the measurement technique described in Experiment 1.

The relative strains of segments 1, 2 and 5, 6 were calculated as $S(1,2) = 1.51 \times 10^{-3}$, and $S(3,4) = 2.48 \times 10^{-3}$, using recorded time shifts. As a result, the ratio between the strains of segments 5, 6 and 3, 4 was calculated to be r' = 0.61.

For reference, the Young's moduli of phantoms 1 and 2 were separately estimated as 7.85 N/cm$^2$ and 4.54 N/cm$^2$ by using the method described in Experiment 1. Therefore, the ratio r between the Young's moduli of phantoms 1 and 2 was 0.58 which is close to 0.61.

In the above examples, the arrival time "windows" for the signals of interest were selected to correspond to targets 1, 2, 3 and 4. It will be recognized that similar windows could have been selected to correspond to the boundaries of the layers shown in FIGS. 5 and 6. Thus, in FIG. 6, windows could have been selected for the upper and lower boundaries 105 and 106, respectively, of the upper layer, and also for the upper and lower boundaries 106 and 107, respectively, of the lower layer. It will be recognized that the invention has application to target bodies which may have more than two layers.

In the two examples, the target bodies were sponges which are elastically compliant, solid form materials which respond to ultra-sonic signals in a manner quite similar to human and other animal tissue. It will be apparent, then, that the invention is not limited in its use to animal tissue and organs. In general, as noted earlier, the invention is contemplated to have application to any substantially solid form material which is compliant, and especially to materials which are both compliant and elastic. In general, the materials should possess sufficient structure to be plastically compliant in a manner such as cheese or elastically compliant in a manner such as rubber, human organs or other human tissue, meat, gels, and the like.

It will be recognized that the foregoing invention may be practiced and modified in many ways. For example, it is well known that ultrasonic transducers are available in matched sets wherein a plurality of matched transducers are assembled side-by-side in a single head. It is contemplated that such multi-channel arrays may be coupled to an animal tissue or other compressible solid material, and that multiple ultrasonic signals may thereby be transmitted into the material simultaneously along an array of radiation axes. Thus, an entire section of the material may be examined by using such an array. Images of strain and/or Young's Modulus may be made.

It will also be recognized that one transducer may be used as a transmitter and that one or more transducers may be offset from the transmitter and used as receivers.

What is claimed is:

1. A non-doppler method of estimating compressibility of a target body which includes the steps of:
   (a) emitting a first pulse of ultrasonic energy along a path into the target body;
   (b) detecting the arrival of a first echo sequence including one or more echo segments from within the target body resulting from said first pulse;
   (c) changing the amount of compression within the target body along said path;
   (d) emitting a second pulse of said ultrasonic energy following said compression change into said target body along said path;
   (e) detecting the arrival of a second echo sequence including one or more of said echo segments arriving from within said target body resulting from said second pulse; and
   (f) measuring the differential displacement of at least one common said echo segment.

2. The method of claim 1 wherein in step (a) a plurality of said pulses are emitted along a corresponding plurality of parallel said paths into the target body, and steps (b) through (f) are performed for each said pulse.

3. The method of claim 1 which further comprises dividing differential displacement by the ratio of the force which changes the amount of compression to the area of the target body to which the force is applied.

4. A non-doppler method for estimating compressibility in a target body including the steps of:
   (a) energizing an ultrasonic source to emit a first ultrasonic signal from said source along an axis into said target body;

(b) detecting from a region within the target body a first echo sequence including a plurality of echo segments resulting from said first ultrasonic transmitted signal;

(c) displacing said target body along said axis relative to the ultrasonic source while maintaining sonic coupling between said ultrasonic source and said target body;

(d) energizing said ultrasonic source to emit a second ultrasonic signal from said ultrasonic source along said axis into said target body;

(e) detecting from the region within the target body a second echo sequence, including echo segments common to said first echo sequence, resulting from said second signal; and (f) measuring the differential displacements of a plurality of the common echo segments.

5. The method of claim 4 wherein the ultrasonic source comprises at least one transducer.

6. The method of claim 4 wherein the ultrasonic source is sonically coupled directly to the target body.

7. The method of claim 4 in which the echo sequences are detected at the ultrasonic source.

8. A non-doppler method for estimating compressibility in organic tissue comprising:

(a) sonically coupling an ultrasonic source to said tissue body;

(b) emitting a first pulse of ultrasonic energy from the source along an axis in said tissue;

(c) detecting the arrival time of a first echo sequence including a plurality of echo segments arriving in response to said first pulse of ultrasonic energy;

(d) transaxially moving the ultrasonic source so as to compress said tissue;

(e) emitting a second pulse of ultrasonic energy from the source along the transmission path in said tissue following said movement;

(f) detecting the arrival time of a second echo sequence, including a plurality of echo segments common to said first echo sequence, arriving in response to said second pulse of ultrasonic energy; and (g) measuring the differential displacement of a plurality of said common echo segments.

9. The method of claim 8 which further comprises dividing each said differential displacement by the ratio of the force causing the movement in step (d) to the area of the tissue to which the force is applied.

10. The method of claim 9, which further comprises: selecting tissue segments within said tissue which extend along the transmission path of the ultrasonic pulses; and measuring in step (g) the differential displacements of common echo segments in the first and second echo sequences which correspond to the proximal and distal ends of said body segments.

11. A doppler method of estimating the compressibility of a target body comprising:

(a) sonically coupling a material with a known Young's Modulus and speed of sound to the surface of the target body;

(b) emitting a first pulse of ultrasonic energy along a path through the material and the target body;

(c) detecting a first echo sequence, including a plurality of echo segments, from within the target body resulting from said first pulse;

(d) forcing the material against the target body sufficiently to compress the target body while maintaining acoustic coupling between the material and the target body;

(e) emitting a second pulse of ultrasonic energy which matches said first pulse of ultrasonic energy along said path through the material and the target body;

(f) detecting a second echo sequence, including a plurality of echo segments common to the first echo sequence, resulting from said second pulse of ultrasonic energy.

12. The method of claim 11 which further comprises detecting the difference in arrival times of at least two of said common echo segments resulting from the two emissions in steps (b) and (e).

13. A non-doppler method of obtaining a strain profile of organic tissue comprising at least two layers of organic tissue defined and separated from each other by boundaries, which comprises the following steps:

(a) sonically coupling an ultrasonic transducer to the surface of the tissue so as to direct ultrasonic signals along a path extending successively through the layers;

(b) energizing the transducer to direct a first ultrasonic signal along said path through said layers;

(c) detecting the arrival times at the transducer of echo segments originating at the proximal and distal boundaries of each said layer and resulting from said first signal;

(d) changing the amount of compression in the tissue layers along said path;

(e) energizing the transducer to direct a second ultrasonic signal along said path through said layers;

(f) detecting the arrival times at the transducer of said echo segments resulting from said second signal; and (g) measuring the differences between the arrival times in steps (c) and (f) for said echo segments.

14. The method of claim 13 in which a layer of material of known Young's modulus and speed of sound is interposed between the transducer and the tissue and is acoustically coupled to both the transducer and the tissue prior to step (a), and steps (a) through (f) are conducted with said path extending through said material and said layers of tissue.

15. The method of claim 14 which further compresses determining the Young's modulus of each said layer of tissue relative to said layer of material.

16. A non-doppler method of studying an internal region of the human body which includes the following steps:

(a) sonically coupling an ultrasonic transducer to the body so as to emit an ultrasonic signal along an axis into the region, and such that movement of the transducer along the axis relative to the region will change the compression of the body between the transducer and the region;

(b) energizing the transducer to emit a first signal along said axis into the body and the region;

(c) detecting the arrival at the transducer of a plurality of spaced echo segments resulting from the first signal and coming from the region;

(d) moving the transducer along the axis relative to the region sufficiently to change the compression of the region while maintaining said sonic coupling;

(e) energizing the transducer to emit a second signal along said axis into the body and said region;

(f) detecting the arrival at the transducer of each echo segment resulting from the second signal which corresponds to an echo segment detected in step (c), above; and (g) determining the strains produced in segments of the region between pairs of said echo segments.

17. A non-doppler method of determining the compressibility of a compressible target body which comprises:

(a) sonically coupling an ultrasonic transducer to the target body which is capable of transmitting an ultrasonic signal along a path into the target body;

(b) transmitting a first such signal from the transducer along the path into the target body;

(c) detecting the arrival times at the transducer of two resulting echo signals from two features within the target body spaced different distances from the transducer along the path;

(d) forcing the transducer against the target body along the path to compress the target body between the transducer and said features;

(e) transmitting a second such signal from the transducer along the path into the target body; and (f) detecting the arrival times at the transducer of the two resulting echo signals from said two features.

18. The method of claim 17 which further comprises computing strain within the target body using the following $$\text{strain} = \frac{(t_{1B} - t_{1A}) - (t_{2B} - t_{2A})}{(t_{1B} - t_{1A})}.$$

where $t_{1A}$ = arrival time of the first echo signal from the proximal feature;

$t_{1B}$ = arrival time of the first echo signal from the distal feature;

$t_{2A}$ = arrival time of the second echo signal from the proximal feature; and $t_{2B}$ = arrival time of the second echo signal from the distal feature.

19. The method of claim 17 which further comprises dividing the force applied in step (d) by the area of the target body against which the force is applied, and also by the value obtained in claim 18.

20. An apparatus for determining compressibility of a target body comprising:

(a) a rigid frame;

(b) a motor attached to the frame;

(c) an axial member having a first end and a second end, said first end coupled to said motor such that the axial position of said axial 9 member can be varied by operating said motor;

(d) an ultrasonic source mounted on the second end of the axial member, said ultrasonic source having a lower surface capable of being sonically coupled to the target body;

(e) a transmitter connected to the ultrasonic source and transmitting signals into the target body, (f) a receiver connected to the ultrasonic source and operable to receive echo sequences from the target body in response to the signals transmitted by the ultrasonic source into the target body, (g) a digitizer connected to the receiver and operable to digitize the echo sequences, and (h) a processor connected to the digitizer and operable to convert the digitized echo sequences into a strain profile.

21. The apparatus of claim 20 which further comprises a layer with a known Young's Modulus and speed of sound, said layer having a top surface coupled to said lower surface and a bottom surface capable of being coupled to the target body.

22. The apparatus of claim 20 wherein the ultrasonic source is a transducer.

23. The apparatus of claim 20 wherein the ultrasonic source is an transducer array.

24. The apparatus of claim 20 wherein the axial member comprises a worm gear.

25. The apparatus of claim 20 which further comprises a data storage medium connected to the digitizer and operable to store digitized echo sequences from the digitizer.

26. The apparatus of claim 20 which further comprises a motor controller connected to the motor and operable such that operation of the motor moves the member in precise amounts.

27. The apparatus of claim 26 wherein the controller includes a programmable computer.

28. The apparatus of claim 20 which further comprises a cross-correlator connected to the digitizer and the processor.

29. The apparatus of claim 20 wherein the processor is programmed to converting echo sequences into an elastic modulus profile.

30. The apparatus of claim 29 which further comprises a monitor connected to the processor and operable to display images of the strain profile of the target body.

31. The apparatus of claim 29 which further comprises a monitor connected to the processor and operable to display images of the elastic modules of the target body.

* * * * *

UNITED STATES PATENT AND TRADEMARK OFFICE
CERTIFICATE OF CORRECTION

PATENT NO. : 5,107,837
DATED : April 28, 1992
INVENTOR(S) : Jonathan Ophir, et al It is certified that error appears in the above-indentified patent and that said Letters Patent is hereby corrected as shown below:

On the title page, under "Other Publications", in the Eisensher reference, delete "Rythmec" and insert there —Rythmee—.

Column 15, line 57, delete "doppler" and insert therefor —non-Doppler—

Column 16, line 46, delete "compresses" and insert therefor —comprises—

Column 18, line 31, delete "sequencies" and insert therefor —sequences—

Column 18, line 51, delete "modules" and insert therefor —modulus—.

Signed and Sealed this

Twelfth Day of October, 1993

Attest:

BRUCE LEHMAN

*Attesting Officer*  *Commissioner of Patents and Trademarks*